(12) United States Patent
Torres et al.

(10) Patent No.: US 7,790,111 B2
(45) Date of Patent: Sep. 7, 2010

(54) OSMOTIC REACTION DETECTOR FOR DETECTING BIOLOGICAL AND NON-BIOLOGICAL REACTIONS

(75) Inventors: Francisco E. Torres, San Jose, CA (US); Jonathan S. Daniels, Austin, TX (US); Meng H. Lean, Santa Clara, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 339 days.

(21) Appl. No.: 11/017,394

(22) Filed: Dec. 20, 2004

(65) Prior Publication Data

US 2006/0134601 A1 Jun. 22, 2006

(51) Int. Cl.
- *G01N 27/00* (2006.01)
- *G01N 13/04* (2006.01)
- *G01N 33/00* (2006.01)

(52) U.S. Cl. .............. 422/82.02; 422/68.1; 436/34; 73/64.47

(58) Field of Classification Search .............. 422/82.02, 422/68.1; 73/64.47; 436/34
See application file for complete search history.

(56) References Cited

U.S. PATENT DOCUMENTS

| | | | |
|---|---|---|---|
| 3,195,346 A | 7/1965 | Ehrmantraut et al. | |
| 3,737,045 A * | 6/1973 | Hashimoto et al. | 210/490 |
| 4,028,931 A | 6/1977 | Bisera et al. | |
| 4,111,203 A | 9/1978 | Theeuwes | |
| 4,455,864 A | 6/1984 | Wallner | |
| 4,475,556 A | 10/1984 | Reiff | |
| 5,005,403 A * | 4/1991 | Steudle et al. | 73/61.71 |
| 5,141,873 A | 8/1992 | Steudle et al. | |
| 5,189,917 A | 3/1993 | Vijayakumar et al. | |
| 5,279,793 A | 1/1994 | Glass | |
| 5,337,747 A | 8/1994 | Neftel | |
| 5,388,449 A * | 2/1995 | LeVeen et al. | 73/64.47 |
| 5,665,904 A | 9/1997 | Böling | |
| 6,267,003 B1 * | 7/2001 | Boris | 73/64.47 |
| 6,268,161 B1 | 7/2001 | Han et al. | |
| 2002/0097489 A1 * | 7/2002 | Kawano et al. | 359/388 |
| 2003/0186453 A1 | 10/2003 | Bell et al. | |
| 2004/0036485 A1 | 2/2004 | Sullivan | |
| 2004/0258753 A1 * | 12/2004 | Demeester et al. | 424/473 |
| 2005/0130319 A1 * | 6/2005 | Biegelsen et al. | 436/514 |
| 2005/0136543 A1 * | 6/2005 | Torres et al. | 436/34 |

(Continued)

FOREIGN PATENT DOCUMENTS

FR 2 672 994 8/1992

(Continued)

OTHER PUBLICATIONS

European Search Report; Application No. EP 04 02 9258; Mailed Mar. 4, 2005.

(Continued)

*Primary Examiner*—Lore Jarrett
(74) *Attorney, Agent, or Firm*—Fay Sharpe LLP (57) ABSTRACT

A method and apparatus for measuring the presence or absence of interaction between at least a first and second material of interest by measuring osmotic pressure changes in an osmotic cell. Changes in osmotic pressure are determined by measuring the amount of compression exhibited by a compressible, semi-permeable material positioned in the cell.

12 Claims, 5 Drawing Sheets

U.S. PATENT DOCUMENTS

2005/0136544 A1    6/2005    Torres et al.

FOREIGN PATENT DOCUMENTS

| JP | 02 226045 A | | 9/1990 |
|---|---|---|---|
| WO | WO 03/061475 A1 | | 7/2003 |
| WO | WO03061475 A1 | * | 7/2003 |

OTHER PUBLICATIONS

Pelrine, R., et al:, *High-Speed Electrically Actuated Elastomers with Strain Greater Than 100%*; Science, vol. 287, pp. 836-839, Feb. 4, 2000.

Wentworth, P. Jr., et al., *Catalytic Antibodies: Structure and Function*, Cell Biochemistry and Biophysics, vol. 35, pp. 63-87, 2001.

Homola, J., et al., *Surface Plasmon Resonance Sensors: Review*; © 1999 Elsevier Science S.A., Sensors and Actuators B, 54 1999), pp. 3-15.

Homola, J., et al., *Present and Future of Surface Plasmon Resonance Biosensors*; Analytical and Bioanalytical Chemistry, Oct. 2003, vol. 377, No. 3, pp. 528-539.

Jung L. S., et al., *Quantitative Interpretation of the Response of Surface Plasmon Resonance Sensors to Adsorbed Films*; © 1998 American Chemical Society; Langmuir, 1998, 14, pp. 5636-5648.

Haemers, S., et al., *An Alternative Method to Quantify Surface Plasmon Resonance Measurements of Adsorption on Flat Surfaces*; © 2002 American Chemical Society; Langmuir, 2002, 18, pp. 2069-2074.

Mamishev, Alexander V., et al., *Interdigital Sensors and Transducers*, Proceedings of the IEEE, vol. 92, No. 5, May 2004, pp. 808-845.

Quake, Stephen R., et al., *From Micro- to Nanofabrication With Soft Materials*, Science, Issues in Nanotechnology, vol. 290, Nov. 24, 2000; pp. 1536-1540.

Reomer, M. et al.,"Microactuators Based on Conducting Polymers", 2002, Analytical Bioanalytical Chemistry, vol. 373, pp. 754-757.

Bourdillon, Jaques, "An Apparatus for the Rapid and Accurate Determination of Low Osmotic Pressures", 1939, Journal of Biological Chemistry, vol. 127, pp. 617-625.

* cited by examiner

OSMOTIC REACTION DETECTOR FOR DETECTING BIOLOGICAL AND NON-BIOLOGICAL REACTIONS

BACKGROUND

The present exemplary embodiments relate to detecting interactions, such as binding, enzymatic or other reactions, in biological and non-biological samples. It finds particular application in conjunction with the reactivity between materials in an array, such as a microarray or array of wells of a microtitre plate, and will be described with particular reference thereto. However, it is to be appreciated that the present exemplary embodiments are also suitable for use in detecting in non-array environments as well.

Researchers are increasingly employing combinatorial chemistry techniques in a variety of areas. In the pharmaceutical industry, the testing of new candidate molecules for binding to a protein, nucleic acid, or other macromolecules of interest is an active area of research with numerous and diverse applications. In addition, there is a great interest in developing new antibodies to catalyze the formation of novel compounds, to catalyze the degradation of unwanted compounds, to modify biological pathways, and to act as therapeutic agents for drug overdose, biological warfare agent exposure, and other conditions caused by particularly potent antigens and poisons.

To test the reactivity in both binding and catalytic reactions of these molecules, researchers are using various techniques, including microarrays and "lab-on-a-chip" type devices. In such techniques, researchers can rely on fluorescent tags to test for reactions between subject molecules. While effective, fluorescent tags must be attached to each candidate compound prior to testing. This process is cumbersome and makes the testing of large numbers of samples time consuming. The article "Catalytic Antibodies: Structure and Function", P. Wentworth and K. Janda (Cell Biochemistry and Biophysics, vol. 35, pp. 63-87, 2001) illustrates many of the problems faced, and gives examples of procedures followed by researchers employing combinatorial chemistry techniques to develop new antibodies. Researchers also use methods that rely on interactions with immobilized reagents, such as studying binding with immobilized reagents using Surface Plasmon Resonance (SPR). While effective, these methods require immobilizing a reagent, which makes the measurement more cumbersome and also introduces uncertainty around whether the immobilization has altered the activity of the reagent.

One technique that researchers are using for real-time, high-throughput monitoring and/or detecting of fast reactions relies on nanocalorimetry-based processes, such as described in commonly assigned U.S. patent application Ser. No. 10/114,611 filed on Apr. 1, 2002 and titled "Apparatus and Method for a Nanocalorimeter for Detecting Chemical Reactions", hereby incorporated by reference. This technique does not require tagging or immobilization of reagents. While effective for samples where a reaction produces sufficient heat in a time scale normally on the order of up to several to tens of seconds, nanocalorimetry is not suitable in applications where the reaction is too slow or too weak to produce a detectable heat. This problem is especially pronounced for those reactions which may require minutes or even hours.

In investigating alternatives, it has been appreciated that osmotic pressure may provide a useful measurement. Particularly, it is known that the osmotic pressure of a solution is a colligative property that depends on the concentration of solute molecules in the solution. For dilute solutions, the osmotic pressure $\Pi$ due to a particular solute obeys the equation $\Pi = cRT$, where c is molar concentration of solute, R is the gas constant, and T is the absolute temperature. Essentially, each mole of solute contributes RT thermal energy to the osmotic pressure.

In a biological test for reaction between a first material and second material of interest, e.g., a protein, and a candidate "probe" compound (or ligand), consider the case where both species are initially present in the same molar concentration, N, in a reaction cell. The use of the terms "first material" and "second material" may be used interchangeably herein with the terms "material 1" and "material 2", respectively, and are intended to be synonymous unless specifically stated. In this initial, unreacted state, the combined concentration of both species is 2N, and each species contributes equally to the osmotic pressure in the cell. If the first material reacts with the second material to form a bound complex molecule, then N moles per unit volume of the first material reacts with N moles per unit volume of the second material to produce N moles per unit volume material 1-material 2 complex. Accordingly, the osmotic pressure due to these two components drops to ½ its previous level prior to binding, since it is now the osmotic pressure of N moles per unit volume of complex.

Conversely, if the reaction of interest is catalytic in nature, for example in the case of a catalytic antibody reaction with an antigen in which the catalytic antibody cleaves the antigen, then N moles per unit volume of material 1 react with N moles per unit volume of material 2 to form 2N moles per unit volume material 2 fragments plus the original N moles per unit volume of material 1. In this case, the osmotic pressure increases by ½. The osmotic pressure is also a parameter which may be monitored over an extended period of time, such as, for example, for up to several hours or more. The osmotic pressure of the products of a reaction does not dissipate, unlike, for example, the heat from an interaction.

There have therefore been attempts to use osmotic pressure to test for reactivity in both biological and non-biological systems. However, these systems have generally examined high concentration environments in which the osmotic pressure is no less than approximately 5,000 to 10,000 N/m². Furthermore, previous systems typically tested for only a single reaction at a time.

In many cases, however, it is desirable to undertake studies at low concentrations, which will generate osmotic pressures at levels much lower than present osmotic-based systems are capable of detecting. One reason the use of low concentrations is attractive, is that the materials may be scarce and/or expensive, making use of larger concentrations impossible or cost prohibitive. Additionally, the quantity of experiments may require the use of low concentrations. In drug screening experiments, for example, researchers may be running anywhere from 1,000 to 100,000 or more different experiments. The use of large concentrations of materials would significantly increase the cost to such a large number of experiments.

Another benefit of low concentration studies is that the use of smaller concentrations provides for more selective reactions. Consider, for example, the study of a binding reaction with a dissociation constant $K_d$:

$$A + B \rightarrow C \quad K_d = \frac{[A][B]}{[C]}$$

In this reaction, A and B bind to form the complex C, and the dissociation constant is written in terms of concentrations denoted by square brackets. This equation assumes ideal solution behavior, but it is sufficient for the purposes herein. In testing for binding, it is often desired to obtain an indication of the magnitude of $K_d$. In many biochemical studies, including drug screening and development studies and proteome-wide investigations of protein-protein interactions, among others, $K_d$ values of interest are typically <1-10 μM, and values from 1-1000 nM—and especially <100nM—are not uncommon and often of particular interest. In order to measure $K_d$, the reaction must be studied at concentrations that are not too distant from the value of $K_d$. At the upper end of this range, titrations may be performed at concentrations of 10 to 100 times $K_d$, but titrations at concentrations near the value of $K_d$ are preferred when possible. Thus, there is a benefit to performing studies at as low a concentration as possible. In particular, there is a benefit to being able to perform studies at concentrations as low as $10^{-6}$ to $10^{-7}$ M. Likewise, it is a benefit to be able to measure kinetics of enzymatic reactions at low concentrations, including enzymatic reactions with slow turnover rates.

One technique that has been proposed for testing samples via osmometry at low concentrations of interest is described in commonly assigned U.S. patent application Ser. No. 10/739,852 filed on Dec. 18, 2003 and titled "Osmotic Reaction Cell for Monitoring Biological and Non-biological Reactions", hereby incorporated by reference. While effective, such a testing procedure requires the use of a sensitive semi-permeable membrane between a reference solution and a solution to be measured, and requires a reference solution. The need for such a membrane can introduce additional cost and difficulties with these systems especially at very low concentrations of interest (>1 mM).

Specifically, measuring osmotic pressure at the levels of interest is difficult when using conventional membranes like those that can be purchased for dialysis. The times for equilibration across the membranes are long at the concentrations of interest (<1 mM), and equilibration of small ions across the membrane may be problematic, perhaps because of charge on the membranes.

Upon a review of the state of art, it has been determined that there is a need for a more direct, simple, and generic assay technique or system for testing large numbers of samples at the low concentration levels of interest without the need for a reference solution or a semi-permeable membrane. The present embodiments disclose such a system and technique.

BRIEF DESCRIPTION

In accordance with a first aspect of the present exemplary embodiments, a method for detecting interactions between at least a first and second material of interest is provided, the method including the steps of providing an osmotic cell with a compressible material positioned therein; introducing into said cell a first material of interest, a second material of interest, and a carrier fluid; and detecting osmotic pressure in said osmotic cell occurring as a result of a change in said osmotic cell of one or more of said first and second materials of interest, wherein said change in osmotic pressure is determined by measuring the compression of said polymer.

In accordance with a second aspect of the present exemplary embodiments, an osmotic cell system for detecting interactivity between first and second materials of interest is provided, the osmotic cell system including a well for containing a mixture including first and second materials of interest and a carrier fluid; a compressible material positioned in said well; and means for measuring compression changes in said compressible material.

In accordance with a third aspect of the present exemplary embodiments, a method for detecting interactions is provided, the method including measuring osmotic pressure changes in individual osmotic cells positioned in an array of osmotic cells, each cell including a compressible material positioned therein; the cells each containing at least first and second materials of interest and a reference solution, wherein the method of measuring includes measuring the compression of said compressible material as a result of osmotic pressure changes in said cells.

DETAILED DESCRIPTION

The present embodiments describe an apparatus and method for measuring osmotic pressure changes for detection of material interactions. In these embodiments, a compressible and semi-permeable material, such as a polymer film or gel, is compressed due to osmotic pressure and changes in this compression can be measured.

As used herein, the terms "first material" and "second material" as well as "material 1" and "material 2" and "materials of interest" are meant to refer broadly to any two or more compounds or molecules (at times referred to herein as "large molecules" or "macro molecules"), of which the potential interactivity is of interest to an investigator. Thus, the terms may refer to without limitation any protein, peptide, polypeptide, nucleic acid, oligonucleotide, compounds bound to beads or matrix materials, antigens or other species that may react therewith. In the present discussion, then, exemplary reference will at times be made to an antibody and an antigen as the first and second materials. However, it is understood that there are numerous interactions which may involve three or more materials of interest, such as, but not limited to, allosteric effects, co-factor plus substrate binding to enzymes, among others. The interactions that such species will undergo include catalytic antibody reactions and antibody binding, among others. It is also to be understood that as used herein "materials" and "materials of interest" are those that do not permeate the compressible film and therefore cause osmotic pressure on the compressible film.

In discussing specific embodiments herein, reference may be made at times to "compressible material", "polymer film", "polymer gel" and similar terms. It should be understood that any discussion or embodiments relating to these individual terms are applicable to any compressible and semi-permeable material having the necessary characteristics described herein, unless specifically stated otherwise. It is also to be understood the permeability of the material would include, but not limited to, a solvent and any buffer molecules, e.g. buffer ions, as well as any co-solvents, e.g. DMSO in a solution used in accordance with the present concepts.

Likewise, reference may be made herein to "reactions" or the "reactivity" between materials. The use of these terms is meant to be read in the broadest sense and include any interaction between two or more compounds or molecules that would change the osmotic pressure in a solution containing the molecules, whether or not the interaction involves the actual making or breaking of covalent chemical bonds. Thus, these and related terms are meant to include, but are not limited to, a broad variety of interactions including binding, enzymatic, and degradation events, among others.

It is to be understood that the first and second materials are not to be construed as limited to the recited materials but are intended to encompass all materials which may be understood to be usable with the described methods and devices. In addition, it should be understood the present methods and apparatuses can be used with more than two materials of interest so long as the concentration per unit volume of species that do not permeate into or through the compressible material changes during reaction between the materials. For convenience and clarity, the focus of the herein described embodiments relate particularly to biological interactions such as, for example, those involving antibodies and antigens, proteins and ligands, proteins and other proteins, enzymes and substrates, and nucleic acids. Therefore, specific reference may be made to the use of an antibody and an antigen as the first and second materials. It is, however, to be understood this is not intended to limit the disclosed concepts to these specific biological reactions, but rather the disclosure may also pertain to other biological as well as non-biological reactions.

In effect, the top surface of the compressible film is acting as a semi-permeable membrane through which the solvent can freely pass but the larger molecules of interest cannot, or at least cannot in the time scale needed for measurement due to kinetic limitations. At the same time, the compressible film responds to the osmotic pressure in a way that can be detected by compressing.

Exemplary embodiments described herein relate to one or more osmotic cells or detectors, and methods for measuring changes in osmotic pressure that may occur during an interaction between two or more materials, including catalytic and binding reactions. When more than a single cell or detector is present, such an arrangement may be thought of as an array of osmotic cells or detectors. It is of course to be appreciated, however, that the same principles relate equally to a single cell or detector. By "cell", applicants mean a location where a solution containing materials of interest is positioned and its osmotic pressure can be determined. Thus, in various embodiments and without limitation, a cell may be a container, depression, well, or simply a spot on top of a detector wherein a drop of solution sits. In fact, if the surface tension of the solution is great enough, no walls or other containment means may be required to contain the solution in the "cell".

As a general description of the embodiments, a compressible material, such as a thin film of polymer (which may be in gel form) or other type of gel, is deposited or otherwise attached to an impermeable substrate and a solution containing a carrier liquid and at least two materials of interest (e.g. proteins) is placed on top of the film covering it. The film is saturated by the solution, but not by the macromolecules contained therein. That is, the polymer film should not only be compressible, but also permeable to the solvent, buffer, and all other species except the "materials of interest" for which a measurement of the osmotic pressure is desired. Of course, there may be a small amount of other species (e.g. contaminants) that cannot permeate into the compressible material, other than the "materials of interest". Preferably then, the amount of any such "contaminant" species is kept at a low enough level to not significantly affect the osmotic pressure. For example, in one embodiment, a hydrogel with high water content is deposited on a surface and subsequently an aqueous solution with dissolved protein is introduced. The hydrogel responds to the osmotic pressure of the solution by compressing. The degree to which the hydrogel compresses is directly related to the number of molecules in the solution that do not permeate the compressible, semi-permeable hydrogel material.

Figure 1A:
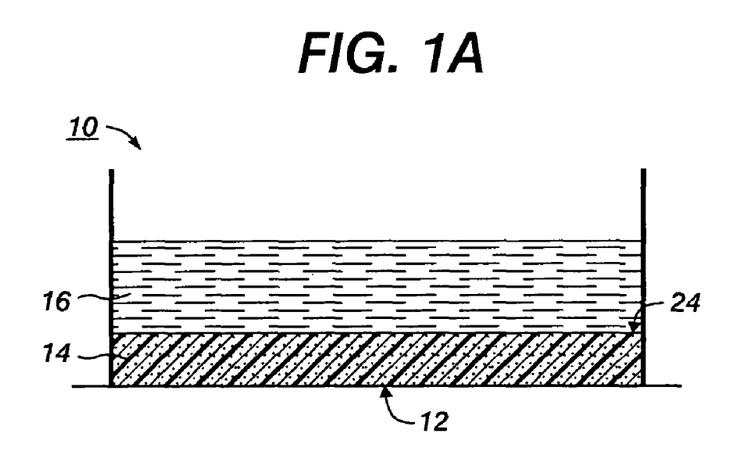
FIGS. 1A and 1B are side views of an osmotic cell according to first and second embodiments.
Figure 1B:
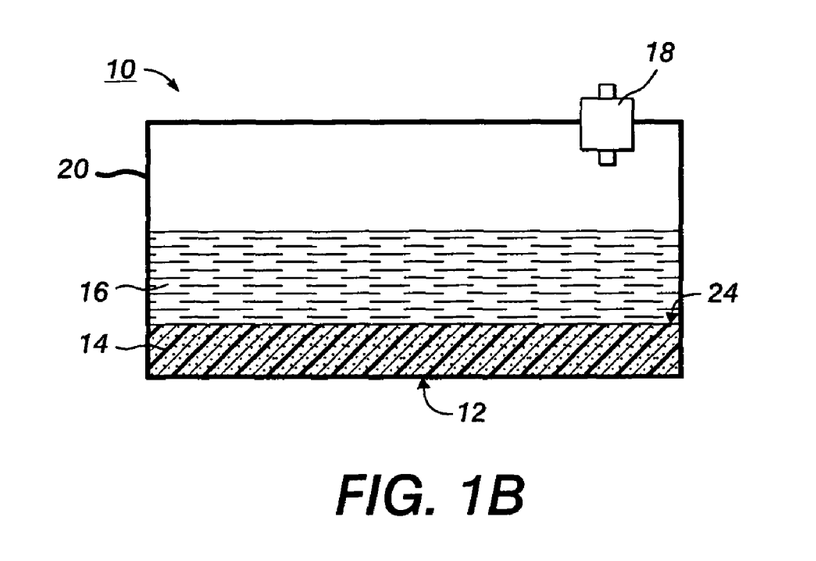

With reference to FIGS. 1A-1B, in a first embodiment, an osmotic cell 10 including a bottom surface 12 is provided. Attached or otherwise positioned on the bottom surface of the cell is a compressible and semi-permeable material, such as a gel or polymer film 14. A reaction solution 16 containing a solvent or carrier fluid and materials of interest is introduced into the cell to cover the polymer film 14. The gel polymer is chosen such that it allows free passage of the solvent but does not allow the adsorption or absorption of the materials of interest and is impermeable thereto.

As mentioned above, it should be understood that the impermeability of the polymer film or gel 14 to the materials of interest does not have to be absolute, but only within the time scale of the measurement. Thus, within the present discussion, a polymer film may be considered impermeable to a material of interest even if the material of interest might permeate the polymer film given a sufficiently long time, since by the time the materials of interest would permeate the film, measurements would have been completed.

It is to be appreciated the configuration of the sensor 10 of FIG. 1A may be altered and will nevertheless still fall within the concepts of the exemplary embodiments. For example, as shown in FIG. 1B, the upper end of the cell 20 may be enclosed, and a fluid input 18, will permit the introduction of fluid. In such an instance, a fluid input 18 may be arranged in any of a number of well known designs, such as a check valve or one way valve, to ensure fluid provided to each cell. A top surface 24 of the polymer is in contact with the reaction solution 16.

Figure 2:
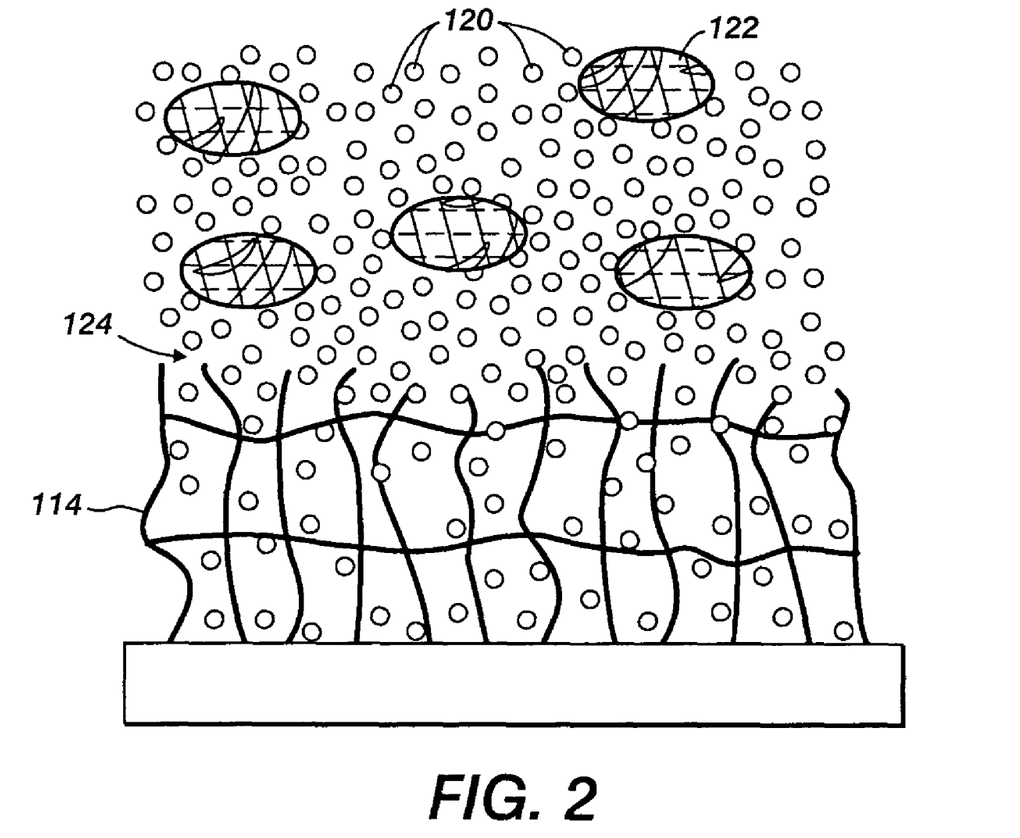
FIG. 2 is depiction of a reaction cell showing a polymer network, a carrier fluid and materials of interest.

FIG. 2 shows a close-up of the carrier fluid molecules 120 permeating through the network of a polymer film 114 while molecules of the materials of interest 122 remain above the polymer because they are too large to penetrate the network.

The osmotic cells 10 can be of any size and made of conventional materials. A suitable type of osmotic cell includes those used in the detecting of biological reactions such as various micro-titre and cell culture plates. The cells can be made of any suitable non-reactive material such as glass or polytetrafluoroethylene. They can be disposable or non-disposable.

The compressible semi-permeable material can be any appropriate material that responds to changes in osmotic pressure by contracting and expanding and will not chemically interact with either the solvent or the materials of interest. Typically, the compressible material will be a polymer film, either crosslinked or uncrosslinked, although other materials such as other types of gels may also be suitable.

Suitable polymers for use in the present embodiments include, but are not limited to, hydrogels including polyacrylamide gels, silicone gels, agarose gels, as well as microbeads (such as those consisting primarily of 1.5 wt % sodium alginate), and other crosslinked and uncrosslinked polymers in water or other solvent. As described above and for convenience, description may be made herein simply to a gel, polymer gel, polymer film, or polymer. It is to be understood that this is merely an exemplary compressible semi-permeable material, and that other materials are not intended to be excluded merely by reference to a particular material.

With continuing attention to FIGS. 1A, 1B and 2, a pressure will build up across a top surface 24 (124) of the polymer layer 14 (114) when there are molecules of two or more materials of interest on the upper side, whereas there are none in the layer itself, nor on the other side of the layer. In effect, the top surface of the polymer layer 24 (124) acts like a semi-permeable membrane, and the interior of the polymer layer acts like a separate "reference compartment" and a pressure develops across that top layer.

The pressure is balanced by compression of the polymer layer until the upward elastic pressure from compression equals the downward osmotic pressure from the solution. The amount of compression is then measured to determine the osmotic pressure (which is directly related to the concentration of molecules of materials of interest). By measuring the change in compression of the polymer both initially and after interaction between the two or more materials of interest, the extent, if any, of interaction between the two materials can be determined. Alternately, if the interaction between the two materials is very fast and an initial compression determination prior to interaction of the materials of interest can not be measured, the amount of compression due to a reference solution can be measured initially. A test solution containing materials of interest with the same combined initial concentration is then added to the osmotic cell. Any changes in compression of the polymer can then be measured to determine the extent of interaction between the materials of interest.

The osmotic pressure depends on number concentration c of large molecules in the solution outside of the compressible, semi-permeable film. In this case c is simply the material of interest concentration in the cell. Then the osmotic pressure $\Pi$ is given by $\Pi=cRT$ in the ideal solution case, where R is the gas constant and T is the absolute temperature. Non-ideal solutions will behave similarly, but the illustrative calculations below assume the ideal solution equation for simplicity.

A strain $\in$ resulting from an applied pressure P is given by $\in=P/E$, where E is the Young's modulus. Combining equations, results in $\in=cRT/E$. Because it is easier to measure larger strains, it is clear that having a polymer film with smaller E (or less stiff film) is advantageous, all other things being equal.

By "compressible", it is meant that the material can be compressed in at least one direction by the osmotic pressure of the solution. It should be noted however that in many cases this will result in an expansion of the material in its other dimensions. This is due to the fact that many elastomers, with Poisson ratios approaching 0.5, characteristically resist a change in volume such that when one dimension is compressed (in our case by osmotic pressure), the other dimensions adjust so the volume of the material remains unchanged. Use of such a material is preferred, and calculations will assume it, but is not required. In fact, it is conceivable that a measurement technique may exploit a material that does not expand laterally, hence the volume of the material (e.g. polymer gel) is reduced when an external pressure is applied and the refractive index of the material changes.

The amount of solution in the reaction cells is selected based on the size of the cells as well as other considerations. The embodiments described herein are well suited to test for reactions at reactant concentrations in the range of approximately $10^{-3}$ to $10^{-7}$ M, and more preferably down to approximately $5\times10^{-6}$ to $10^{-7}$ M, assuming a solution amount of approximately 20 nanoliters to 100 microliters. Thus, in an exemplary embodiment, the cells may be containers or depressions approximately 1 mm on a side and approximately 100 microns deep for a total volume of 0.1 µl. Of course, the embodiments should not be construed as being limited to such ranges or geometric shapes, and the principles of operation can be applied to larger or smaller cells, solution amounts, and concentrations of species therein. In the presently described embodiments, the volume of each cell is typically from about 20 nL to about 100 µl, although as described below, measurements can be conducted using drops of solution having a volume of about 2 nL on a detector.

Each reaction cell may be filled via any known method, such as through the use of micropipettes or any other fluid delivery system. One contemplated method is through the use of a delivery system similar to that used in high end ink jet printing devices including acoustic drop ejection systems. Such systems are known in the art and may be readily adapted for use with the exemplary embodiments of present embodiments. For example, when the cells have an open top end, then it is straightforward to use commercially available, robotic liquid sample delivery systems to deliver samples to these chambers.

Since the thickness of the polymer gel film is preferably small, nominally around 50-100 nm, the equilibration of the solution within the gel and the solution outside of the gel will be much faster than with a membrane separating two chambers, as in prior methods. Also, temperature variations across the dimensions of the film will be much smaller than with a macroscopic membrane, minimizing unwanted effects from temperature variations. This technique can be integrated with microfluidics for lab-on-a-chip types of applications.

One of the benefits of the present embodiments is to enable measurements and detect interactions at very small sample (i.e. mixture) volumes. In this respect, both the compressible film and a suitable detector can be made small to enable measurements with small sample volumes. For example, a suitable sensor for use in the present embodiments is Texas Instruments Spreeta™ Biosensors, which have an advertised flow cell volume of 20-100 nL. The Spreeta™ Biosensors use surface plasmon resonance (SBR), which, as discussed below, is one suitable method to detect compression of the compressible film. Another suitable arrangement according to the present processes is to position small drops, for example drops with a radius of approximately 100 microns, on a compressible film and measure the compression of the film area covered by the drop. The surface tension of the solution will keep the drop from spreading out. A 100 micron radius drop has a volume of approximately 2 nL.

Consider the measurement of a protein-protein reaction in the case where each protein is at a concentration N before any interaction (such as mixing) and equal volumes of each protein solution are combined. Assume the solutions can be modeled using ideal solution thermodynamics for this analysis. It should be noted that the embodiments measure osmotic pressure regardless of whether the solutions can be described by ideal solution thermodynamics. The assumption of ideal solution behavior makes the analysis easier, but it should not be viewed as limiting the claims. If all of the proteins bind, the osmotic pressure will be that due to the concentration N/2 of bound protein pairs, whereas if the proteins do not bind, the osmotic pressure will be twice as large.

Hence, measuring the osmotic pressure could be used to determine if a binding event is taking place, as in a screening experiment, or to detect the level of binding, perhaps for a titration in determining $K_d$. For the purpose of illustrating one way to do the measurement, consider performing the steps as follows: First, the osmotic pressure of one species at concentration N can be measured. Then a sample of a second species at a concentration N can be added. If desired, its osmotic pressure can be measured separately if desired to make sure it is the same or to account for any difference. If the osmotic pressure does not change upon combining the two samples, then a interaction between the materials of interest is not taking place. If the osmotic pressure drops, then binding is taking place, causing the concentration of species that do not cross the osmotic barrier to decrease from N to a lower value. If all protein pairs bind due to high affinity, the lower value of the concentration after adding the second species is N/2, as stated above. If cleavage reaction takes place, then the osmotic pressure will increase. Note that all concentrations are number concentrations, e.g. moles per unit volume, as is appropriate for discussing osmotic pressure.

Figure 3:
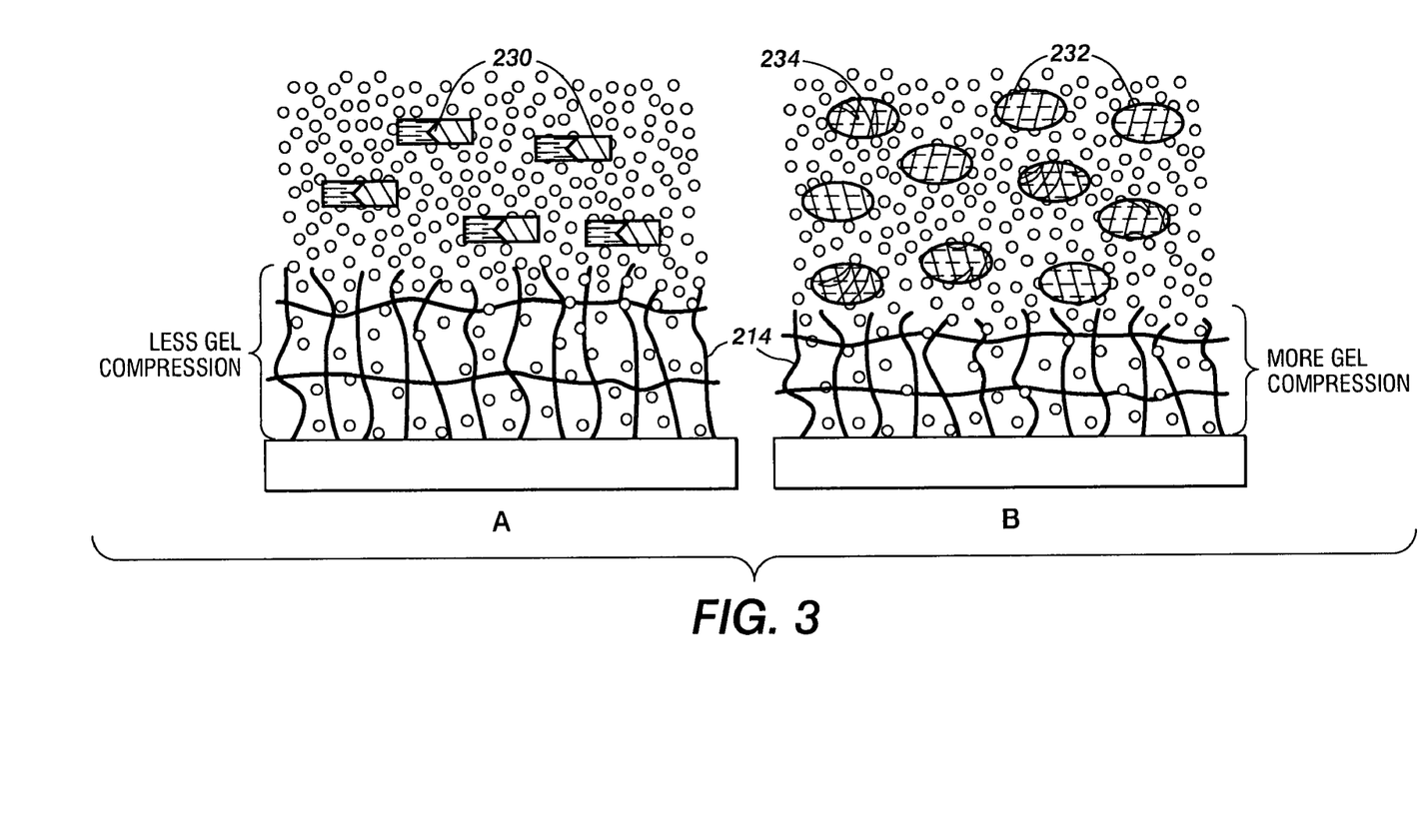
FIG. 3 is a depiction of an osmotic cell showing different degrees of polymer compression due to reaction or absence of interaction between materials of interest.

FIG. 3 shows two osmotic cells. In cell A, less compression of the polymer 214 is experienced when the materials of interest bind to create bound species 230, due to the reduction of total concentration of independent, impermeable species in the solvent. In cell B, the compression of the polymer network is greater when the materials of interest do not bind or otherwise interact due to greater concentration of independent, impermeable species, namely, molecules of the first and second materials 232 and 234.

Measurements can also be done in combination with a reference experiment to help distinguish background effects from interactions due to the proteins of interest. Background effects can arise due to physical effects including temperature drifts or differences in buffers, or they can be noise or drift in the sensing electronics. Consider a test for interaction between protein A and protein B. In the reference measurement, the same protein A can be combined with a macromolecule C that does not interact with A but has the same osmotic pressure against the buffer as protein B. By comparing the signals when A and B are combined vs. A and C, background effects can be reduced or eliminated, making it easier to distinguish the desired signal. As an example, C could be a dextran molecule with a molecular weight large enough that it does not penetrate into the thin gel film, where protein A would not react with dextran. Dextran is relatively inert, has good water solubility, and has low toxicity. Molecular Probes, Inc. sells dextrans with molecular weights from 3000 Da to 2,000,000 Da. Of course, other non-reactive reference materials may also be used.

Doing measurements in parallel, e.g. high throughput measurements, with samples from microtitre plates, etc., is anticipated. Similarly, measuring in "biochip" platforms using microfluidics to bring sample to a measurement area, doing the measurement, then sweeping the sample away and introducing another one is also anticipated.

In an alternate embodiment, the polymer gel does not need to be impermeable to all materials of interest as well as products formed therefrom. Rather, the present embodiments can be used to determine the occurrence and extent of reaction between first and second materials so long as the molar concentration of impermeable components changes when a reaction in the reaction cell occurs. For example, it may be the case where a catalytic antibody reacts with an impermeable molecule, breaking it up into parts that are all permeable. In such a case, there are permeable products, but the number of impermeable components change from two (i.e. the catalytic antibody plus the impermeable molecule) to one (catalytic antibody). This reaction will result in osmotic pressure change. This is also the case for a reaction that changes permeable reactants into impermeable products. On the other hand, if a catalytic antibody cleaved an impermeable reactant into two separate molecules, one permeable and the other impermeable, then there would not be a shift in osmotic pressure because the molar concentration of impermeable entities would not change.

Conversely, any binding or catalytic reaction between the antibody and the antigen (can) alter the number of total impermeable solute entities in the cell when both species are impermeable, which in turn changes the osmotic pressure exerted on the polymer gel. For example, and with initial concentrations as described above, if the antigen and antibody undergo a binding reaction to form an antigen-antibody complex molecule, then N moles per unit volume of the antigen compound react with N moles per unit volume of antibody to produce N moles per unit volume of antigen-antibody complex. Accordingly, the osmotic pressure due to these two components drops to ½ its previous level An opposite result occurs if there is a catalytic reaction between the antigen and the antibody in the cell that cleaves the antigen. In this case, N moles per unit volume of antigen molecule may react with N moles per unit volume of antibody to form 2N moles per unit volume of antigen fragments plus the original N moles per unit volume of catalytic antibody, increasing the osmotic pressure in the cell. It should be noted that the above description assumes equal initial molar concentrations for both the antibody and the antigen. This is not necessary, however, and the described embodiments can readily be extended to systems for which the molar concentrations of antibody and antigen are unequal.

As previously noted, these osmotic pressure changes due to reactions between the antigen and the antibody can be described in the ideal solution case by the equation:

$$\Pi = cRT,$$

where $\Pi$ is osmotic pressure, c is molar concentration of large molecule solute, R is the gas constant, and T is the absolute temperature. When the reaction is carried out in the cell 10 described above, these differential pressure changes manifest themselves in a compression of the polymer. The present embodiments are particularly well-suited to measure osmotic pressure changes for reactions in which the impermeable, large molecule species are initially present in concentrations in a range of approximately $5 \times 10^{-3}$ to $5 \times 10^{-7}$ M. At these concentrations, $\Pi$ typically ranges from about 1.2 to 2600 N/m², based on typical measurement temperatures in the range of 5° C. to 40° C. The embodiments are, however, also compatible with solutions having higher concentrations as well.

The compression of the polymer may be measured using any of a number of different techniques, which may be applied to each reaction cell of an array.

In one embodiment, one possible method for measuring the film thickness (and thus the compression from its original thickness) is the technique of surface plasmon resonance (SPR). For further discussion of SPR and the formulae employed below, see J. Homola et al., Sensors and Actuators B, 54 (1999) p. 3-15; J. Homola, Analytical and Bioanalytical Chemistry, October 2003, v.377, no.3, p. 528-539; L. S. Jung et al., Langmuir, 1998, 14, 5636-48, or S. Haemers et al., Langmuir 2002, 18, 2069-74.

Figure 4:
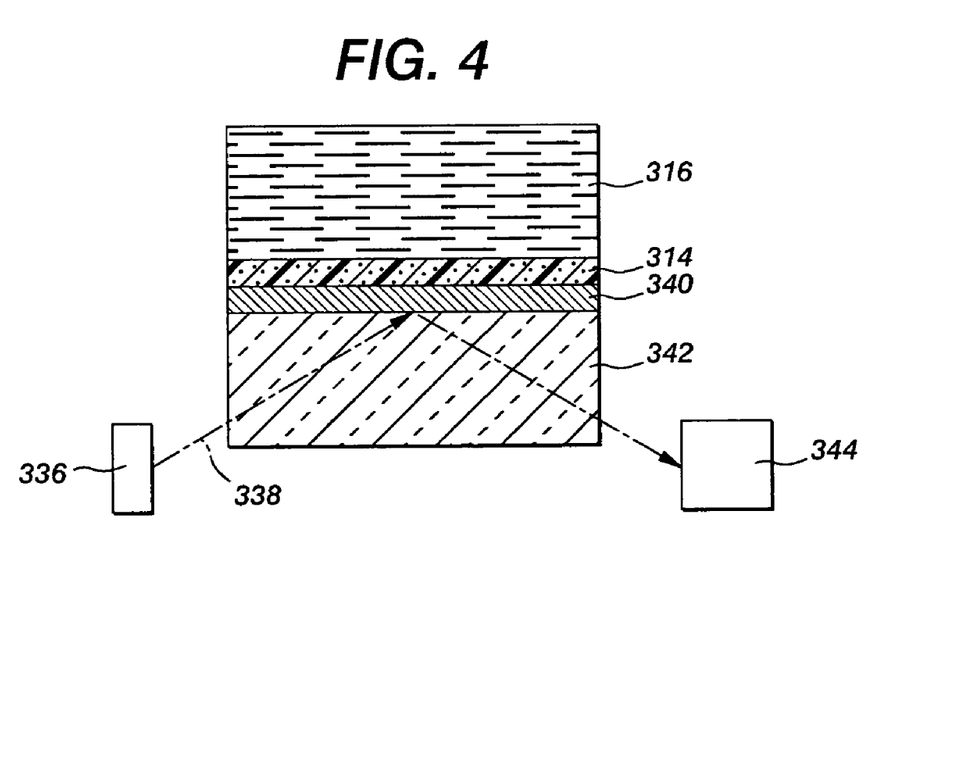
FIG. 4 is a side view of an osmotic cell and SPR based detection system for measuring polymer compression.

SPR measures the refractive index with high sensitivity in the vicinity of a metallic surface. As seen in FIG. 4, the usual configuration uses a light source 336 which generates a light beam 338 reflected off of a thin film of gold or silver 340 to a sensor/computer arrangement 344. At a particular incidence angle, energy from the light can couple into a surface electromagnetic excitation called a plasmon, and a steep reduction in the reflected intensity is observed. The exact angle at which this occurs is a sensitive function of the refractive index on the non-incident side of the metal. An SPR operation is a non-invasive technique. The sensitivity of the surface plasmon resonance angle to the refractive index comes about because of the exponentially-decaying evanescent wave that penetrates the metal film when the light is reflected.

One method for making SPR-based measurements is to shine a monochromatic beam, adjust the apparatus angle to match the resonance angle, then introduce an external agent, and adjust the angle again, noting the difference in the two angles. It is widely reported that a change in refractive index of $10^{-6}$ can be measured in this manner. The exact method by which the SPR effect is measured is not critical. The method just described has been reported to be highly sensitive based on the small angular differences that can be measured.

The refractive index (RI) measured by SPR is an exponentially-weighted value due to the evanescent wave source of the phenomenon. The characteristic length scale of the exponential weighting is half of the penetration length of the incident wave, which is usually about one third of its wavelength (the exact value depends on the complex dielectric constant of the metal and dielectric constant of the surrounding media).

FIG. 4 is a depiction of an arrangement for making SPR measurements on a reaction cell according to the present embodiments. As with the embodiments above, a reaction solution 316 containing a carrier solvent and materials of interest is positioned on top of a compressible polymer layer 314. The compressible polymer in turn is positioned on top of a gold or silver film 340 with a transparent substrate underneath it. The angle of an impinging monochromatic beam is measured before and after reaction to determine the amount of compression of the polymer.

The monochromatic light source may be a laser, diode or other appropriate light-emitting device, and the detector may be a split-diode detector, or other detector, which will perform the required detection of the movement of the reflected light.

The measured refractive index is $\eta_{eff}=(2/l_d)\int\eta(z)\exp(-2z/l_d)dz$ (integrated from z=0 to infinity) where $l_d$ is the penetration length. Assuming a Poisson ratio approaching 0.5 and that the polymer layer is unconstrained laterally, osmotic pressure will cause the polymer to compress vertically and expand laterally without significantly changing the refractive index of the polymer. Thus, the change in refractive index measured by SPR will be due to the change in polymer thickness d that occurs. Assuming a sharp transition between the two layers, $\Delta\eta_{eff}=[\exp(-2_f/l_d)-\exp(-2d_i/l_d)]*(\eta_s-\eta_p)$ where $d_f$ and $d_i$ are the final and initial thicknesses. With $d_f=d_i+d_i*\in=d_i(1+\in)$ where $\in$ is the strain (given by $\in=\Pi/E$ where $\Pi$ is the applied pressure (osmotic in origin in this case) and E is the Young's modulus) and assuming that $\in$ is small, it can be shown that $\eta_{eff}=\exp(-2d_i/l_d)*(-2d_{i\in/ld})*(\eta_s-\eta_p)$. To maximize the absolute value of $\eta_{eff}$, it can be shown that $d_i$ should be chosen to be as close to $l_d/2$ as possible.

To summarize, the $\eta_{eff}$ which is measured by SPR is given by $-[2d_i\Pi*\exp(-2d_i/l_d)*(\eta_s-\eta_p)]/(E*l_d)$, where $\Pi$ is the osmotic pressure, E is the Young's modulus of the polymer layer, $d_i$ is the initial thickness of the polymer layer, $l_d$ is the penetration length of the incident light (which depends on the complex dielectric constant of the metal and dielectric constant of the surrounding media), and $\eta_s$ and $\eta_p$ are the refractive indices of the solution and polymer layer, respectively. Clearly, it is desirable to have a very small modulus and large refractive index difference compared with the surrounding (aqueous) solution.

Just to give a rough estimate of sensitivity, take SPR detection limit of $10^{-6}$, $l_d=200$ nm, $d_i=50$ nm, E=50 kPa, and ($\eta_s-\eta_p$)=0.036. The polymer film properties are based on a reported value of a 20% polyacrylamide gel having a 50 kPa modulus, and a dn/dC value for polyacrylamide of 0.17 mL/g (Polymer Handbook). These values are merely exemplary and not presented as optimal, and are simply provided as a starting point. Based on these, a pressure variation of 4.6 Pa can be detected, which corresponds to 1.9 µM variation in the concentration of large molecules (using $\Pi$=cRT). As discussed below, gels with lower moduli are known in the art.

It can be shown that maximum sensitivity occurs when the polymer thickness is half of the penetration depth $l_d$. This maxima is fairly broad, however, meaning that tight manufacturing tolerances are not required. Repeating the calculation with $d_i=100$ nm, half the penetration depth, the minimum detectable pressure variation is 3.8 Pa, which corresponds to 1.5 µM concentration.

It is expected that significantly smaller moduli can be obtained careful engineering of the polymer layer. It is reported that the Young's modulus of elastomers, for instance, can be tuned over two orders of magnitude by controlling the amount of cross-linking. See Science, Vol 290, Issue 5496, 1536-1540, 24 Nov. 2000. For our application, a large ratio of the difference in refractive index (as compared to the solution) divided by the Young's modulus is desirable. Moduli for such gels can vary significantly. Here is a brief sampling of values for Young's modulus of polymer layers from the literature:

28.9 kPa—proprietary silicone gel (available from Geltec Co., Ltd.)

10 kPa—3% agarose hydrogel 1.04 kPa, 6.95 kPa—microbeads composed primarily of 1.5 wt % sodium alginate.

40 kPa—crosslinked acrylamide in 80% water (as reported in PNAS; Jan. 6, 2004; vol. 101, no. 1, 23-26)

50 kPa—20% polyacrylamide gel

Another method to measure the compression of the polymer gel is Total Internal Reflection Fluorescent Microscopy (TIRFM). The basic concept of TIRFM is similar to SPR, requiring only an excitation light beam traveling at a high incident angle through a material, such as glass, in contact with solution. Refractive index differences between the glass and water phases regulate how light is refracted or reflected at the interface as a function of incident angle. At a specific critical angle, the beam of light is totally reflected from the interface, rather than passing through. The reflection generates a very thin electromagnetic field (usually less than 200 nanometers) in the aqueous medium, which has an identical frequency to that of the incident light. This is the same as the evanescent wave in SPR. A layer of metal can be used at the interface, but it is not strictly required. The energy of the evanescent wave can be absorbed by fluorophores and re-emitted by them at their characteristic wavelengths.

This technique could be used to measure small displacements in the top of the polymer layer if fluorophores are embedded in the polymer. The reflected light beam is incident on the non-polymer side, and the evanescent wave is coincident with the polymer layer. It would be advantageous to have such fluorophores present only near the top surface of the polymer layer. As the layer compresses, the fluorophores will be brought closer to the surface of reflection, and hence into a region of higher intensity of the evanescent wave, and hence will fluoresce more brightly. The optimal thickness of the polymer layer will be related to the penetration length of the evanescent wave.

Another method to measure compression of the compressible material is Total Internal Reflection Spectroscopy. Total Internal Refection Spectroscopy is a combination of TIRFM and IR absorption spectroscopy. A beam of light is confined by total internal reflection, with the aforementioned evanescent wave penetrating the other side (the side of the polymer layer exposed to the solution, in this case). If the incident light is at a wavelength that the polymer absorbs, then lower intensity will be observed at the output. The wavelength of incident light can be varied to produce a spectrum.

This approach could be used to detect compression of the polymer layer by measuring changes in absorption amount. As the polymer layer compresses then the amount of the polymer per unit area in the direction of propagation of the evanescent wave will change, e.g. becoming less for a polymer that maintains a constant volume when compressed. If the polymer volume were reduced when compressed, then an effect might still be observed because the distribution of the polymer close to the surface would change. It is expected that the variation measured would be quite small, and multiple reflections would be necessary to measure an effect.

Many other measurement approaches are also possible. These include ellipsometry, reflectometry, capacitance, Fabry-Perot resonator structures, and interferometry. The lack of mention of a particular technique does not eliminate it as a potential method for the present embodiments.

Figure 5:
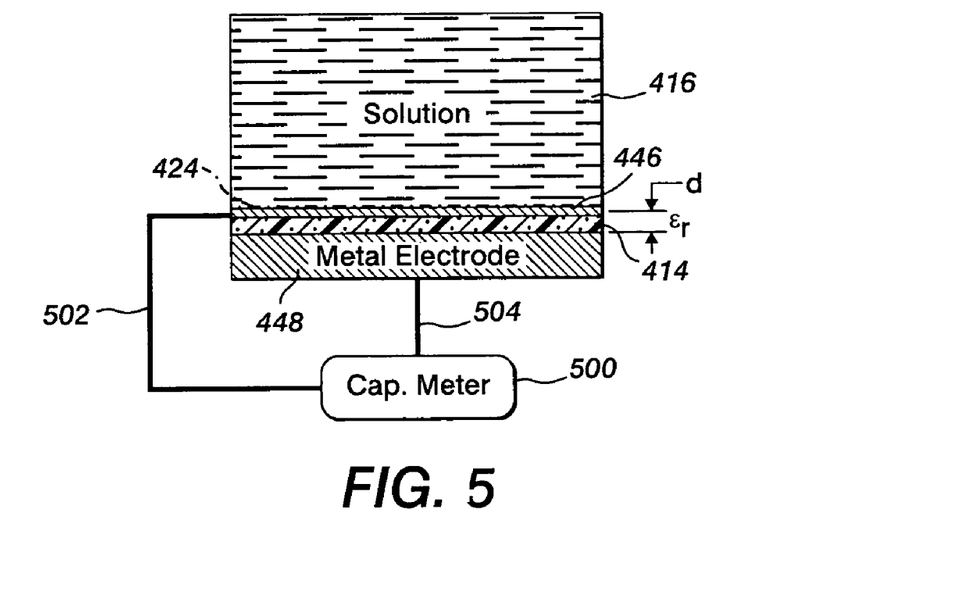
FIG. 5 is a side view of an osmotic cell and a resistive/capacitive measurement based detection system for measuring polymer compression.

Another embodiment measures the capacitance of the gel as a function of compression. As shown in FIG. 5, this embodiment employs a pressure sensitive gel 414 between two spaced apart conductors/electrodes 446 and 448 in operative connection with a capacitance/resistance detector 500 and exposed directly to a reaction mixture 416 at an interface surface 424. The capacitance detector is connected to conductors 446 and 448 via conductor lines 502 and 504, respectively. The gel 414 in FIG. 5 is sufficiently crosslinked so reactants, for example an antigen and antibody, cannot penetrate the gel. In this case, the osmotic pressure difference between the surface of the gel and its interior will compress the gel.

The compressible layer is deposited on top of a solid substrate. An electrode beneath the compressible layer acts as one plate of a capacitor. The compressible layer can rest directly on top of the metal layer, or else an insulating layer (not shown) can separate them. It is desirable that such an insulating layer, if present, be as thin as possible. On the top of the compressible layer, a partial layer of conducting material, such as a metal, is applied. It is preferable that the metal not block complete access of the solution to the compressible layer, or else the compressible layer will not respond to osmotic pressure as it should. One preferable arrangement for the top conducting layer is an interconnected mesh. A conductor should be provided to make external contact with the top conducting layer.

If the conducting layer is metal, this layer could be made by sputtering metal, taking care to deposit enough to interconnect but not so much that the compressible layer is sealed from the top to the solution. It could also be implemented as a pre-made metal mesh that is secured to the top of the compressible layer. A layer of conducting polymer could be used as the top layer, whether by a grafted copolymer manufacturing approach or simply by placing a thin film of prefabricated conducting polymer on top of the insulating polymer (in this case, the conducting polymer layer could replace or augment the functionality of the compressible layer in that it allows water to pass but not large molecules such as proteins). Other approaches for depositing a thin metal layer on top of the polymer layer may also be used.

The relative thickness of the compressible layer can then be measured by measuring the capacitance between the bottom and top electrodes, if the relative dielectric constant of the polymer is known using the equation $C=\epsilon_r\epsilon_0 A/d$. In the envisioned implementation, the compressible layer would be an elastomer and so $\epsilon_r$ would not change when the film is compressed, only d. In the envisioned implementation, the absolute difference d is not of importance, but rather the percent difference in d between two time points. This can be obtained by taking a percent change of capacitance measurements, regardless of the actual values of d and $\epsilon_r$.

Presented are some calculations to demonstrate that this technique is sufficiently sensitive to measure small osmotic pressures. Assume the cross-sectional area to be 10 mm² (roughly the bottom area of a well in a 384-well plate), the thickness of the compressible layer to be 50 nm, and the relative dielectric constant of the compressible layer to be 60, which is reasonable with a high water content gel. Further assume it is assumed that due to the incomplete metal coverage on the top, the capacitance value is 20% (the value that it would have if the layer were complete).

When the osmotic pressure is applied, the compressible layer spreads laterally in addition to being compressed vertically. Note that such a property is not strictly required, but most soft polymer materials have this elastomeric property. It follows that this spreading, which increases the area A at the same time that the distance d decreases, is important to consider. To conserve volume, if the vertical strain $(d_{final}-d_{initial})/d_{initial}=-\epsilon$, then additionally $(A_{final}-A_{initial})/A_{initial}=\epsilon$. The fractional change in capacitance $(C_f-C_i)/C_i$ is just $(A_{final}d_{final})/(A_{initial}d_{final})-1$. Assuming constant volume and small strain, this reduces to $2\epsilon$. Thus, the fractional change is capacitance is just twice the strain. If no such lateral spreading occurs and the volume of the compressible layer is reduced, then the fractional change in capacitance is simply the strain—$(d_{initial}/d_{initial})=-\epsilon$. Thus, having an elastomeric material (with Poisson ratio as close to 0.5 as possible) is desirable. Having a soft material, in the sense of a low Young's modulus (high strain for small applied pressure) is even more desirable. The technique described here measures the compressible layer thickness but the modulus converts between that change in thickness and the actual osmotic pressure that is being applied.

With the values given above, the initial capacitance is 21 nF. Assuming that one can measure a 10 pF variation in that, one can measure strains of 0.00024. The strain is simply given by Π/E, where Π is the applied pressure (osmotic in origin here) and E is the Young's modulus of the compressible layer. Assuming a gel with Young's modulus of 50 kPa and recalling that Π=ΔcRT, then a protein concentration of 4.9 uM corresponds to a strain of 0.00024.

Thus, we would expect sensitivity to be in the low uM range with this method, depending on the details of manufacture, materials used and measurement. A low value for Young's modulus is desirable so that a small osmotic pressure corresponds to a high displacement of the compressible layer. Polymers gels having moduli in the 10s of kPa and below are reasonable to manufacture, and it would be desirable to have an even lower modulus. Of course, those having higher moduli can be used, with a corresponding reduction in sensitivity.

The gel thickness does not influence sensitivity to first order, if the measurement is one of percent change in capacitance (which is the most robust method against manufacturing variations).

Analysis reveals that the smallest detectable strain is half the smallest fractional capacitance change that is measurable, if an incompressible (elastomeric) polymer layer is used. It will be somewhat larger if the material is not elastomeric. In addition, a non-elastomeric polymer may change dielectric constant when it is compressed. Such a polymer layer may still be viably used, but one would have to know the details of such changes and take them into account.

One alternative approach that should be mentioned is the measurement of capacitance by fringing fields, similar to commercial stud-finders, in this approach, two electrodes would be placed under the polymer layer. A series of interdigitated electrodes could also be used, based on the same physical principles. The capacitance between these two electrodes is measured, and is sensitive to the dielectric constant of the surrounding material. Assuming water as a solvent, if the polymer is compressed vertically, for example, now water is closer to the electrodes and the measured capacitance will be larger (assuming the dielectric constant of water is larger than that of the polymer layer).

A metallic layer on the top surface might enhance this effect, but is not strictly necessary. Such a metal layer would not be electrically connected to anything, relaxing the manufacturing difficulty somewhat.

An analysis of the sensitivity of such an approach is complicated and only realistically performed by computer simulations. A good reference for this approach is A. V. Mamishev et al, Proceedings of the IEEE, Vol. 92, No. 5, May 2004, 808-845.

In yet another embodiment, having an arrangement such as shown in FIG. 5, the gel 414 is designed to have a conductance that depends on compression, making it possible to monitor the amount of expansion or compression, and therefore the osmotic pressure, by measuring the resistance across conductors/electrodes 446, 448 by capacitance/resistance detector 500. As an example of such a gel, one can use a polymer gel material and load it with carbon black particles near the percolation threshold for the particulate phase. Elastomeric materials loaded with conductive particles near their percolation threshold exhibit a conductance having a strong dependence on the applied pressure, this dependence arising because compression increases the number of particle-particle contacts. Conductive particles other than carbon black can be used. Preferably, the gel is made from a material that is not soluble, or only slightly soluble, in the fluids being tested, as a gel that is largely or completely swollen in the fluids being tested will remain completely swollen at different osmotic pressures, eliminating the change in shape with osmotic pressure that is required for this embodiment. It is to be appreciated the component designated capacitance/resistance detector 500 is designated as a capacitance/resistance detector for convenience in the discussion. However, it is not required that the component be able to perform both functions, but rather it may perform the function appropriate for the particular embodiment.

As in the previous embodiment, suitable gels will be designed to have a conductance that depends on compression, making it possible to monitor the amount of compression or expansion, and therefore the osmotic pressure, by measuring the resistance across electrodes 446, 448.

Figure 6:
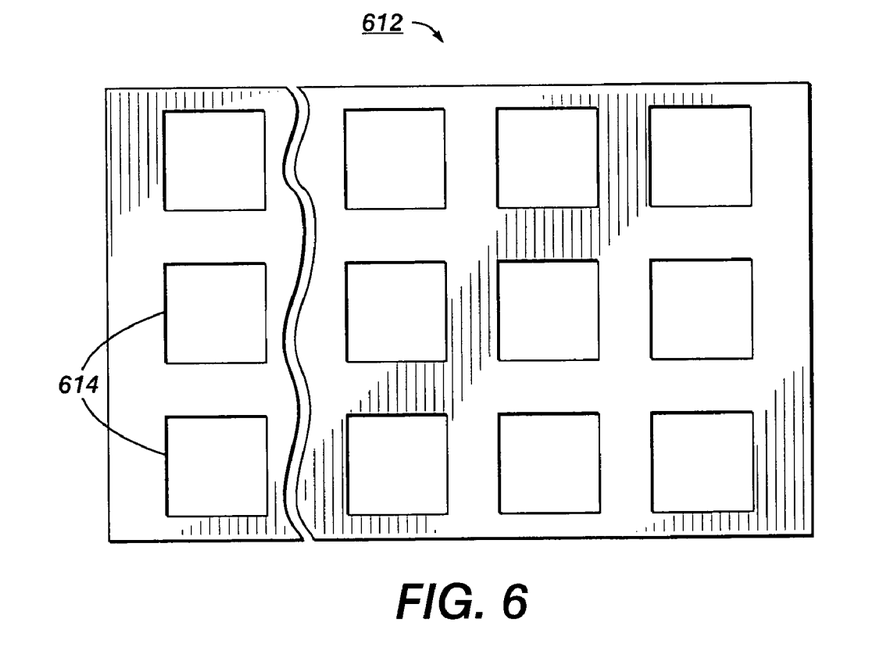
FIG. 6 is a top view of an array of osmotic reaction cells.

Expanding upon the array concepts described herein, reference is made to FIG. 6, which illustrates an array 612 of individual reaction cells 614 according to any one of the embodiments discussed above. Such an array allows for the testing of a large number of samples using the same or different materials of interest and probe compounds in individual reaction cells. Therefore, it is possible to not only perform massive parallel investigations, which is very beneficial for use in areas which employ combinatorial chemistry, but it is also possible to perform distinct investigations by filling reaction cells of the array with distinct solutions and/or reaction mixtures.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A system for detecting interactions between at least a first material of interest and a second material of interest, said system comprising:
    one cavity for receiving and retaining at least said first and second materials of interest and said carrier fluid, said cavity having a bottom surface;
    a compressible, semi-permeable polymer gel material comprising carbon black particles;
    said compressible, semi-permeable material having an initial uncompressed state and a second compressed state indicating compression responsive to osmotic pressure acting on said compressible, semi-permeable material;
    a mixture including at least first and second materials of interest and a carrier fluid is positioned above the semi-permeable material;
    a top conductor and a bottom conductor, wherein the top conductor is positioned on a top surface of said compressible, semi-permeable material, and the bottom conductor is positioned at a bottom surface of said compressible, semi-permeable material, wherein said compressible, semi-permeable material has a conductance dependent on its compression state;
    an interface surface positioned between said mixture and said top conductor;
    a capacitance detector
    configured to monitor compression changes in said compressible, semi-permeable material by measuring the capacitance across said pair of conductors; and
    a pair of conductor lines connected to said top and bottom conductors and said capacitance detector, wherein said compressible, semi-permeable material, said mixture, said top and bottom conductors, said interface surface, said capacitance detector, and said pair of conductor lines are positioned inside said cavity.

2. A system according to claim 1, wherein said compressible, semi-permeable material is impermeable to at least one of said first and second materials of interest during the time scale needed for a measurement operation to be completed by the system and is permeable to said carrier fluid.

3. A system according to claim 1, wherein said compressible, semi-permeable material has a thickness of from 50-100 nm.

4. A system according to claim 1, wherein said compressible, semi-permeable material has an E modulus of from about 1 to 50 kPa.

5. A system according to claim 1, wherein pressure changes as low as 3.8 Pa can be detected in said material.

6. A system according to claim 1, wherein changes in concentration as low as 1.5 µM of at least one of said first and second materials of interest can be detected.

7. A system according to claim 1, wherein said compressible, semi-permeable material maintains a constant or near-constant volume under compression.

8. A system according to claim 1, wherein a volume of the mixture is less than 10 µL.

9. A system according to claim 1, wherein a volume of the mixture is less than or equal to 1 μL.

10. A system according to claim 1, wherein a volume of the mixture is less than or equal to 100 nL.

11. A system according to claim 1, wherein a volume of the mixture is less than or equal to 20 nL.

12. A system according to claim 1, wherein said system includes an array of said locations, and at least two of the locations of the array utilize different first and/or second materials of interest.

* * * * *